United States Patent
Fridolin et al.

(10) Patent No.: US 9,103,789 B2
(45) Date of Patent: Aug. 11, 2015

(54) METHOD AND DEVICE FOR DETERMINING CONTENT OF THE MIDDLE AND PROTEIN BOUND UREMIC TOXINS IN A BIOLOGICAL FLUID

(75) Inventors: Ivo Fridolin, Tallinn (EE); Fredrik Uhlin, Linkoping (SE); Jana Holmar, Tallinn (EE); Risto Tanner, Tallinn (EE); Jurgen Arund, Saue vald (EE)

(73) Assignee: TALLINN UNIVERSITY OF TECHNOLOGY, Tallinn (EE)

( * ) Notice: Subject to any disclaimer, the term of this patent is extended or adjusted under 35 U.S.C. 154(b) by 0 days.

(21) Appl. No.: 13/807,688

(22) PCT Filed: Jun. 28, 2011

(86) PCT No.: PCT/EE2011/000008
§ 371 (c)(1),
(2), (4) Date: Apr. 9, 2013

(87) PCT Pub. No.: WO2012/000521
PCT Pub. Date: Jan. 5, 2012

(65) Prior Publication Data
US 2013/0193347 A1    Aug. 1, 2013

(30) Foreign Application Priority Data

Jun. 28, 2010 (EE) .................................. 201000056
Dec. 10, 2010 (EE) .................................. 201000085

(51) Int. Cl.
*G01N 21/64*    (2006.01)

(52) U.S. Cl.
CPC .................................. *G01N 21/6486* (2013.01)

(58) Field of Classification Search
CPC ............ G01N 21/645; G01N 21/6458; G01N 21/6486; G01N 33/48; G01N 33/57438
USPC ....................................................... 250/459.1
See application file for complete search history.

(56) References Cited

U.S. PATENT DOCUMENTS

| | | | |
|---|---|---|---|
| 2003/0231294 A1* | 12/2003 | Wariar et al. | 356/39 |
| 2006/0188402 A1* | 8/2006 | Xie et al. | 422/82.08 |
| 2007/0281288 A1* | 12/2007 | Belkin et al. | 435/4 |
| 2008/0015434 A1* | 1/2008 | Rubinstein et al. | 600/431 |
| 2008/0199972 A1* | 8/2008 | Sellrie | 436/501 |

* cited by examiner

*Primary Examiner* — Marcus Taningco
(74) *Attorney, Agent, or Firm* — Gearhart Law LLC (57) ABSTRACT

This invention relates to a novel method and a device for determining middle and protein bound uremic toxins in the biological fluids. More specifically, the present invention relates to an optical method utilizing fluorescence, preferable fluorescence of the spent dialysate, and a specific model, including a unique set of optical spectral components at certain wavelengths, to determine, preferable on-line, the concentration of the middle and protein bound uremic toxins such as beta2-microglobulin (B2M), and indoxyl sulfate (IS).

8 Claims, 8 Drawing Sheets

METHOD AND DEVICE FOR DETERMINING CONTENT OF THE MIDDLE AND PROTEIN BOUND UREMIC TOXINS IN A BIOLOGICAL FLUID

TECHNICAL FIELD

This invention relates to a novel method and a device for determining and quantitative concentration measurements of compounds in the biological fluids such as middle and protein bound uremic toxins in the biological fluids. More specifically, the present invention relates to an optical method utilizing fluorescence, preferable fluorescence of the spent dialysate, and a specific model, including a unique set of optical spectral components at certain wavelengths, to determine, preferable on-line, the concentration of the middle and protein bound uremic toxins such as beta2-microglobulin (B2M), and indoxyl sulfate (IS).

BACKGROUND OF THE INVENTION

The uremic syndrome is attributed to the progressive retention of a large number of compounds, which under normal conditions are excreted by healthy kidneys. These compounds are called uremic retention solutes, or uremic toxins, when they interact negatively with biologic functions. The uremic syndrome is a complex "intoxication" of the retention of waste products resulting in multifactorial problems where disturbances in several metabolic functions are reflected in clinical problems. Several organs and organ systems are affected: cardio-vascular system (hypertension, pericarditis and heart failure), peripheral nervous system (polyneuropathy), central nervous system (poor memory, loss of concentration and slower mental ability), hematology (anemia, bleeding tendencies), coagulation, immune status (immuno-supression), nausea, vomiting etc.

European Society of Artificial Organs (ESAO) and European Uremic Toxin Work Group (EUTox) have done a lot of research and have had a great success to identify uremic toxins and to connect uremic toxins with the clinical status of the renal patients (Vanholder, De Smet et al. 2003).

In the medical literature the uremic toxins are divided into three groups: 1) small molecules (MW<500 Da); 2) middle molecules (MW>500 Da); 3) protein-bound solutes.

Different uremic toxins have effect to the patient by many different ways and extent, and to ensure the best survival, quality of the treatment and the quality of life for the dialysis patients monitoring of several uremic toxins is essential.

Clinically, the most discussed molecules connected to uremic toxicity are the following: Small molecular weight solutes (MW<500 g/mol): Urea, Creatinine, Uric acid, Guanidine-ADMA (asymmetric dimethylarginine), Phosphate.

Middle molecules (MW>500 g/mol): β2-microglobulin, Cytokines (Interleukin 6), Parathyroid hormon (PTH)—(at the same time belongs to the protein-bound group).

Protein-bound solutes: Indoxyl sulfate, Homocysteine, P-cresol, AGE products, Hippuric acid.

A more extensive overview about the small molecular weight uremic toxins can be found in (Vanholder et al 2003). An important conclusion can be made that dialysis treatment assessment by monitoring solely a marker urea is not enough. In this context, a method and a device for quantitative concentration measurements of water soluble small molecular weight substances such as urea, creatinine, and uric acid in the spent dialysate is described in the earlier works. (WO2009071102A1, Apr. 12, 2007. Ivo Fridolin, et al., and EE201000049, 27 May 2010, Fridolin et al)

Nowdays, due to availability of highly convective dialysis therapies like HDF which target to remove more efficiently the middle molecules (MM) (MW>500 g/mol), the quality should be assessed by a marker molecule which belongs into MM uremic toxin group (e.g. β2-microglobulin), or behaves like MM as can be expected by several protein bounded uremic toxins. The above middlemolecular compounds have a pathogenic role or are markers of the most frequent long-term complications and causes of death in HD patients such as dialysis related amyloidosis, cardio-vascular disease, secondary hyperparathyroidism, inflammation and malnutrition. Reduction of the accumulation and lower long-term levels of these compounds may prevent or delay the appearance of such complications. Significant reductions in the incidence of carpal tunnel syndrome and signs of dialysis-related amyloidosis have been reported in two large retrospective studies as a result of high-flux membranes and of convective and mixed dialysis strategies inducing lower chronic β2-microglobulin levels. (Tattersall, Martin-Malo et al. 2007)

A short description about the most relevant uremic toxins in the middle molecule and in the protein-bound solute group, stressing relevance and importance for monitoring, is given below.

β2-microglobulin (B2M) (MW 11 818 D) is the light chain of HLA class I complex and as such is expressed on all nucleated cells. B2M is normally found in low concentrations in the plasma. In end stage renal failure its concentration increases markedly secondary to reduced renal elimination. Uremia-related amyloid is to a large extent composed of B2M and is essentially found in the osteoarticular system and in the carpal tunnel Uremia related amyloidosis becomes clinically apparent after several years of chronic renal failure and/or in the aged. B2M has become a frequently used marker for the dialytic removal of middle molecules. Behavior of B2M during dialysis is, however, not necessarily representative of that of other middle molecules. Hemodialysis with large pore membranes results in a progressive decrease of predialysis B2M concentrations and in a lower prevalence of dialysis-related amyloidosis and/or carpal tunnel syndrome. In a subanalysis of the Hemodialysis (HEMO) Study, serum B2M levels were directly related to patient outcome. European Best Practice Guidelines (EBPG) have pointed out that despite no surrogate molecule has been identified yet with the characteristics of an ideal marker for MM uremic toxins, B2M is representative in its kinetic behaviour of other MM and peptides of similar size, and may be used as a marker for such molecules. (ERA-EDTA 2002)

Cytokines are small molecules and connected with uremia- and dialysis-induced chronic inflammation. There is about 150 cytokines known, but about 300 cytokines are supposed to exist. Uremic toxins are Interleukin-1-beta, Interleukin 6 and Tumor Necrosis Factor Alpha. The accumulation of TNF-Alpha may contribute to the development of neurologic and hematologic complications in uremia. Interleukin-6 (MW 24 500 D) is regulating immune system and increases with bacterial and virus infection.

Homocysteine (Hcy) (MW 135 D), a sulphur-containing amino acid, is produced by the demethylation of dietary methionine. Retention results in the cellular accumulation of S-adenosyl homocysteine, an extremely toxic compound, which competes with S-adenosyl-methionine and inhibits methyltransferase. Moderate hyperhomocysteinemia is an independent risk factor for cardiovascular disease. Hcy increases the proliferation of vascular smooth muscle cells, one of the most prominent hallmarks of atherosclerosis.

P-cresol (MW 108 D) is cleared by the kidney and metabolized by the liver. P-cresol is uremic toxin involved in the depression of immune function. The protein binding is high and removal with dialysis treatment is low.

AGE products (3-Deoxyglucosone, Fructoselysine, Glyoxal (ethanedial), Methylglyoxal, N-Epsilon-(Carboxymethyl)lysine, Pentosidine (MW 342 D)) are retained not only in renal failure but also in diabetes mellitus and aging, where they are held responsible for tissular damage and functional disturbances.

Hippuric acid (MW 179 D) may be derived from the intake of coffee, fruits, or vegetables that contain quinic acid. This compound is converted to benzoic acid by bacterial activity in the gut; the benzoate is conjugated with glycine by the liver to form hippurate. In addition to dietary intake of hippuric acid and its precursors, patients on hippuric acid receive a further load of hippuric acid precursor in the form of benzyl alcohol, which may be used as a preservative in some heparin solutions and in multidose formulations of erythropoietin. Hippuric acid may enhance drug toxicity and the toxicity of other protein-bound uremic solutes due to competition for protein binding. It has been related to insulin resistance and glucose intolerance. (Yavuz, et al. 2005) Hippuric acid has been mentioned as one compound suitable for monitoring utilizing UV-absorbance (U.S. Pat. No. 6,666,840, 23 Dec. 2003, Falkvall et al). However, the latest research has been demonstrated that hippuric acid monitoring by the above described method can be hardly realized. (Trifonov 2009) For this reason new approaches are needed.

Indoxyl sulfate (IS) (MW 251 D) is metabolized by the liver from indole, which is produced by the intestinal flora as a metabolite of tryptophan. The production of indole in the gut may be greater in uremic patients than in normal subjects because of the effect the uremic milieu has on the composition of intestinal flora. IS is a circulating uremic toxin stimulating glomerular sclerosis and interstitial fibrosis and its removal by PD or by oral sorbent administration retards the progression of intact nephron loss. Indoxyl sulfate is one of the well known substances of a group of protein-bound uremic retention solutes that increases the rate of progression of renal failure. In plasma, IS is a protein-bound uremic solute that induces endothelial dysfunction by inhibiting endothelial proliferation and migration in vitro. Some studies suggest that IS is also involved in oxidative stress. In hemodialyzed patients, serum levels of IS are associated with levels of pentosidine, a marker of carbonyl and oxidative stress; in vitro, indoxyl sulfate increases reactive oxygen species production in tubular cells, and increases NAD(P)H oxidase activity in endothelial cells. Indoxyl sulfate impairs osteoblast function, induces abnormalities of bone turnover and strongly decreases the levels of glutathione, one of the most active antioxidant systems of the cell. (Wishart D S, Knox C et al. 2009)

Indole-3-acetic acid (I3AA) is a breakdown product of tryptophan metabolism and is often produced by the action of bacteria in the mammalian gut. Some endogenous production of I3AA in mammalian tissues also occurs. It may be produced by the decarboxylation of tryptamine or the oxidative deamination of tryptophan. I3AA frequently occurs at low levels in urine and has been found in elevated levels in the urine of patients with phenylketonuria. Using material extracted from human urine, it was discovered by Kogl in 1933 that Indoleacetic acid is also an important plant hormone. Specifically I3AA is a member of the group of phytohormones called auxins. I3AA is generally considered to be the most important native auxin. Plant cells synthesize I3AA from tryptophan. I3AA and some derivatives can be oxidised by horseradish peroxidase (HRP) to cytotoxic species. I3AA is only toxic after oxidative decarboxylation; the effect of I3AA/HRP is thought to be due in part to the formation of methylene-oxindole, which may conjugate with DNA bases and protein thiols. I3AA/HRP could be used as the basis for targeted cancer, a potential new role for plant auxins in cancer therapy. (Wishart D S, Knox C et al. 2009) $\beta$2-microglobulin is mainly determined by ELISA assay method. Although the method is automated as an automatic bio-analyzer, the merits of the ELISA itself reside in mass detecting discrepancy and complicacy of the method. It cannot be applied in routine or household detecting because it requires professionals to operate, is expensive, and there is hard to store the detecting agents. Great care has been taken to ensure the quality and reliability of the method but however, it is possible that in certain cases unusual results may be obtained due to high levels of interfering factors.

Many of AGE products can be determined using liquid chromatography, but the disadvantages is that the measurements are very complex. Nearly each of AGE-s needs special handling, special sample pretreatment method, chromatography, and detection procedure different from handling of any other AGE product. Altogether a lot of different facilities, hardly available reagents as well as operation by highly qualified professionals are required.

Other MM and protein bound uremic toxins are determined mostly utilizing the high performance reverse liquid chromatography (HPLC) method. For example, indoxyl sulfate has been determined by fluorescence detection (excitation 280 nm, emission 340 nm), and hippuric acid has been analyzed by ultraviolet detection at 254 nm in the serum and in the spent dialysate. (Dhondt, Vanholder et al. 2003) The demerits of this method include: 1) separation of the compounds may be difficult due to similar properties which affects the test accuracy; 2) the operation is complex, needs lots of agents and should be operated by professionals; 3) the sample needs pretreatment for deproteinization; and 4) the necessary equipment is expensive.

Another method for determination of drugs by fluorescence is proposed in WO2005111586, 13 May 2004, Babichenko et al. The technology utilizes spectral fluorescence signature (SFS) technology for on-site drug detection and quantification. The methos is suitable for measurements of untreated street samples under the assumption that SFS of the stored known library substances match with the compounds in the untreated street samples. This is hardly fulfilled for the biological fluids containing many unknown substances. Also, a need for measurements of three dimensional fluorescence spectra used for comparison with a database including three dimensional fluorescence spectra of the stored known library substances makes the solution technically complex and complicated for implementation as a small, simple and robust. Similar approach, utilizing optical multi-dimensional signatures, is described in US20050079628, 9 Oct. 2003, Nekrasov Viktor et al aiming analysis of substances and materials by optical methods, particularly in multicomponent mixtures. The described method for assaying multi-component mixtures requires also standard samples with a known content having similar drawbacks as forementioned approach.

Another method for determination of the amount of waste products in the dialysis liquid during dialysis treatment to control the dialysis machine in order to adapt the dialysis treatment to the patient is described in U.S. Pat. No. 6,666,840, 23 Dec. 2003, Falkvall et al, and in the reference. (Fridolin, Magnusson et al. 2002) The measurements of a concentration of a certain substance or a combination of substances in the dialysis liquid are obtained continuously or regularly on a sample from outgoing dialysis liquid from a dialyzer during dialysis treatment. The measurements are performed spectrophotometrically by means of UV-radiation (wavelength in the range 180-380 nm). At least one parameter for the dialysis treatment is adjusted depending on the measurement of the concentration of the substance or combination thereof. The merits of the described method are that it does not need blood samples, no disposables or chemicals, and is fast. However, the described method is general and does not specify methodology to measure exclusively a single compound and is meant to apply only for dialysis monitoring. Moreover, no results about the concentration measurements are presented. More exact description about the uric acid and urea measurements using the abovementioned method is given in a scientific papers. (Uhlin, Lindberg et al. 2005), (Uhlin, Fridolin et al. 2005)

Another method relates to a method for dialysis monitoring method and apparatus using near infrared radiation, described in WO9819592, 14 May 1998, RIO GRANDE MEDICAL TECH INC. The merits of the described method are similar to that of the UV-radiation. However, the described method measures urea and creatinine by utilizing near infrared radiation spectrometry with different technical and optical considerations. For near infrared radiation spectrometry the principal component analysis using calibration and prediction stage is described in U.S. Pat. No. 5,886,347.

Another method, described in RU2212029, 10 Sep. 2003, VASILEVSKIJ A M et al, relies on the Beer-Lambert law and utilizes the millimolar extinction coefficients of the components in the spent dialysate. The example given in this invention describes concentration determination of urea, phosphate, creatinine and uric acid. However, the example is given only for one dialysis session which is a serious limitation and can not be applied for the general use. Furthermore, urea and phosphate do not absorb UV-radiation as incorrectly claimed in this application, and thus concentration measurement of urea and phosphate is impossible using this invention. Moreover, because of several unknown chromophores in the spent dialysate the concentration measurement of creatinine is not applicable using the Beer-Lambert law.

Recently, a method and a device for quantitative concentration measurements of water soluble small molecular weight substances such as urea, creatinine, and uric acid in the in the spent dialysate is proposed (EE201000049, 27 May 2010, Fridolin et al).

However, all above mentioned methods assess water soluble small molecular weight compounds, and not uremic toxins in the middle molecule and in the protein-bound solute group. Laboratory and chromatographic analysis for the latter are rather complicated and utilise disposables or chemicals, thus non-fitted for on-line, continuous patient or clinical treatment (e.g. dialysis) monitoring.

Thus, there is a need for a new method which can directly and easily determine middle and protein bound uremic toxins in the biological fluids, like in the serum, urine, saliva and in the spent dialysate, suitable for monitoring, which avoids the disadvantages caused by the existing analysis methods.

SUMMARY OF THE INVENTIONS

The purpose of the invention is, therefore, a new method and a device for determining content of the middle and protein bound uremic toxins in the biological fluids. More specifically, the present invention relates to an optical method utilizing fluorescence of the biological fluid, preferable fluorescence of the spent dialysate and concentration calculation algorithm containing the transforming function to determine on the samples or on-line the concentration of the substances, which can be effected directly at the bed-side. The method and device determines the concentration of the substances in-vitro or on-line utilizing a measuring cuvette (cell) suitable for specified measurements.

Another object of the present invention is to provide a practical optical method and device determining quantitatively concentration or removal of the middle and protein bound uremic toxins in the biological fluids. The determined values can be represented directly and easily on the monitor or screen printed. The method and device does not require any chemical disposables, neither expensive separation techniques, and can be easily made and mass-produced providing an environment-friendly optical method.

A still further object of the present invention is to provide a method for assessing routine clinical monitoring in order to face risks of higher mortality in patients (e.g. in dialysis).

A still further object of the present invention is to provide a novel, rapid, convenient and safe method for detecting concentration of substances in a liquid sample. The liquid sample can be directly dropped on the detecting cuvette for in-vitro measurements or sent a flowing stream of fluid through a flow-through cell for on-line monitoring. The method is suitable for household use when being applied to detect the concentration of substances in the biological fluids.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposed, and not to limit the scope of the inventive subject matter.

BRIEF DESCRIPTION OF THE DRAWINGS

The present invention will be described below in the detailed description with reference to the accompanied drawings where.

DETAILED DESCRIPTION OF THE INVENTIONS

Figure 1:
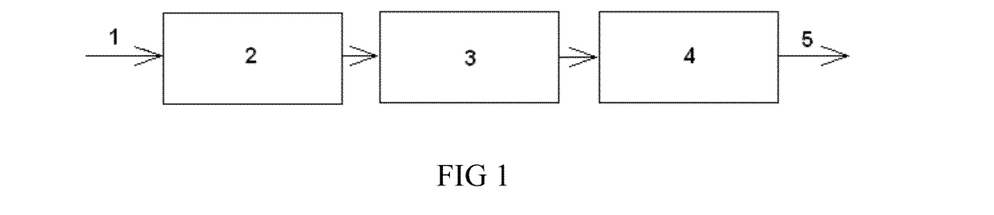
FIG. 1 shows a block diagram of one embodiment of the invention applied for determining content of the middle and protein bound uremic toxins in the spent dialysate during dialysis.

The device for determining content of the middle and protein bound uremic toxins 5 (e.g. B2M) in a biological fluid 1 (see FIG. 1) comprises:

an optical module 2, comprising a fluorimetrical system, comprising a light source and a light detector, and a measuring fluorimetrical cuvette for holding a sample of the biological fluid 1 so that the light can be led onto the sample and the fluorescence signal can be detected from the sample; and a signal processing module 3 consisting of a data acquisition module and a signal processing module incorporating concentration or removal calculation algorithm with the transforming function, and a data representing module 4.

The light source can be either a broadband light source or a narrowband light source. If broadband light source is used, either a broadband detector and a filter can be used, or narrowband detectors. According to one embodiment, the light source is operating in the particular optical region (wavelength range 190-890 nm).

According to one embodiment, the fluorescence light detector is operating in wavelength range of 190-900 nm. The detectable fluorescent light may be emitted directly by the measurable substance in the biofluid or the emission may be intermediated by some other natural or purposefully added constituents of the biofluid through some energy transfer mechanism between molecules in the fluid under the consideration.

The measuring cuvette can be, e.g., adapted for in-vitro measurements, or designed for the on-line measurements.

According to one embodiment, the spectra processing module is adapted to execute a concentration or removal calculation algorithm comprising a transforming function calculating the concentration of certain substance in the biological fluid.

The transforming function is based on the regression analysis in order to transform fluorescence signal, F (dimensionless), into a certain uremic toxin concentration [mg/L]. In the presence of a linear relationship the transforming function has the form "uremic toxin concentration [mg/L]=F*Slope+Intercept".

The data representing module is adapted to execute a program for data representation and comprises or is connected to a data visualization module, e.g., a monitor, a display, or a printing device.

Example

Concentration measurement of the certain substances, a middle molecule beta2-microglobulin (B2M), and the protein bound uremic toxin indoxyl sulfate (IS) in the spent dialysate is given as an example of the present invention.

Subjects: Eight uremic patients, one female and seven males, were included in the study. All patients were on chronic three-weekly on-line HemDiaFiltration (ol-HDF) at the Department of Nephrology, University Hospital of Linkoping, Sweden. The dialysis machine used was a Fresenius 5008 (Fresenius Medical Care, Germany). The dialyzers used were in all treatments FX 800 (Fresenius Medical Care, Germany), with an effective membrane area of 1.8 m2, with an ultra filtration coefficient of 63 ml/h mmHg. The duration of the ol-HDF treatments varied between 180 to 270 minutes, the dialysate flow was 500 mL/min, the blood flow varied between 280-350 mL/min. All patients were dialyzed via artery-venous fistulas using a "two-needle" system. The auto sub system mode for calculation of the on-line prepared substitution volume varied between 12.2 to 29.7 liters per session.

Sampling: Samples from the drain tube were taken at (min) 9, 30, 60, 120, 180 and at the end of ol-HDF session if longer than 180 min. One sample was taken from the dialysate/ultrafiltrate collection tank after careful stirring and weighing was performed. If a self-test of the dialysis machine occurred during the planned sampling time, the sample was taken when the UV-absorbance curve reached baseline level again which occurred within 2-3 minutes. Pure dialysate was collected before the start of a dialysis session, used as the reference solution, when the dialysis machine was prepared for starting and the conductivity was stable.

Determination of concentrations of B2M in the spent dialysate/ultrafiltrate was performed at the Chemical Laboratory, University Hospital in Linköping. Concentration of IS was determined by fluorescence signal during HPLC analysis in Tallinn Technical University, Technomedicum, Department of Biomedical Engineering.

Spectrofluorophotometer (SHIMADZU RF-5301) was used for the fluorescence measurements. Fluorescence analysis was performed over an excitation wavelength range of 220-900 nm (preferably 220-500 nm), emission wavelength range of 220-890 nm (preferably 220-800 nm) and with excitation increment 10 nm. An optical cuvette with an optical path length of 0.4 and 1 cm was used. The obtained fluorescence values were processed and presented by software Panorama fluorescence and the final data processing was performed in EXCEL (Microsoft Office Excel 2003).

On the basis of the results the linear correlation coefficient (R) and the R-squared value (R2) was determined. The accuracy (BIAS) and precision (SE) were calculated for the new method using concentrations from the laboratory as the reference.

Figure 2A:
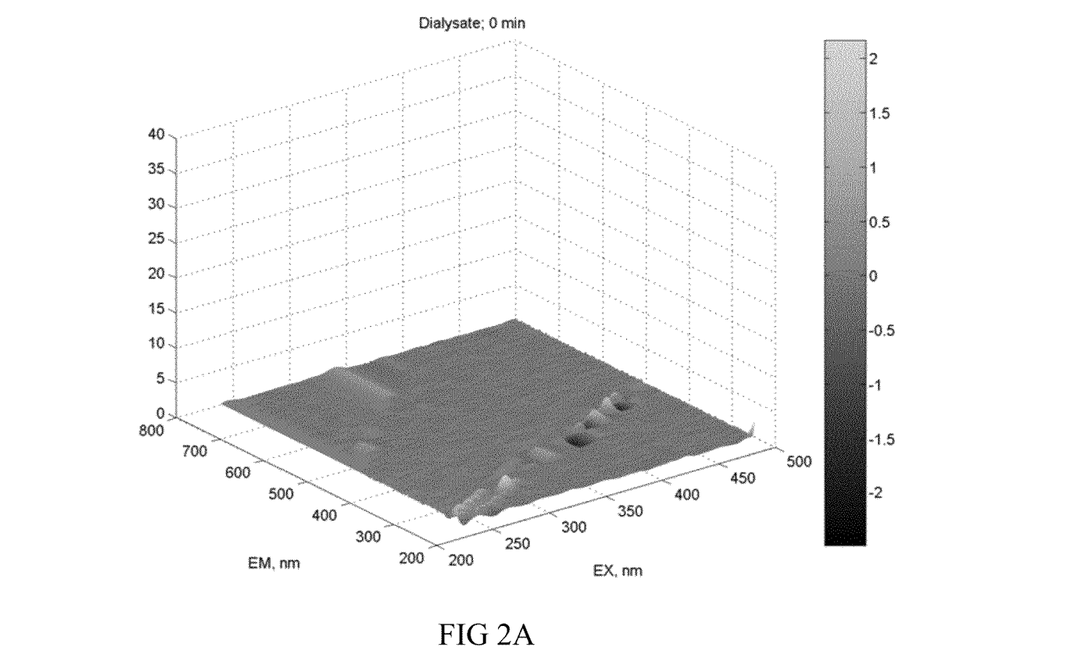
FIG. 2 shows the examples of fluorescence spectra obtained over the excitation wavelength range of 220-500 nm and emission wavelength range of 250-800 nm (A) on the pure dialysate sample; (B) on the spent dialysate sample taken at 10 min after the start of a dialysis session; and (C) on the spent dialysate sample taken at 207 min after the start of a dialysis session.
Figure 2B:
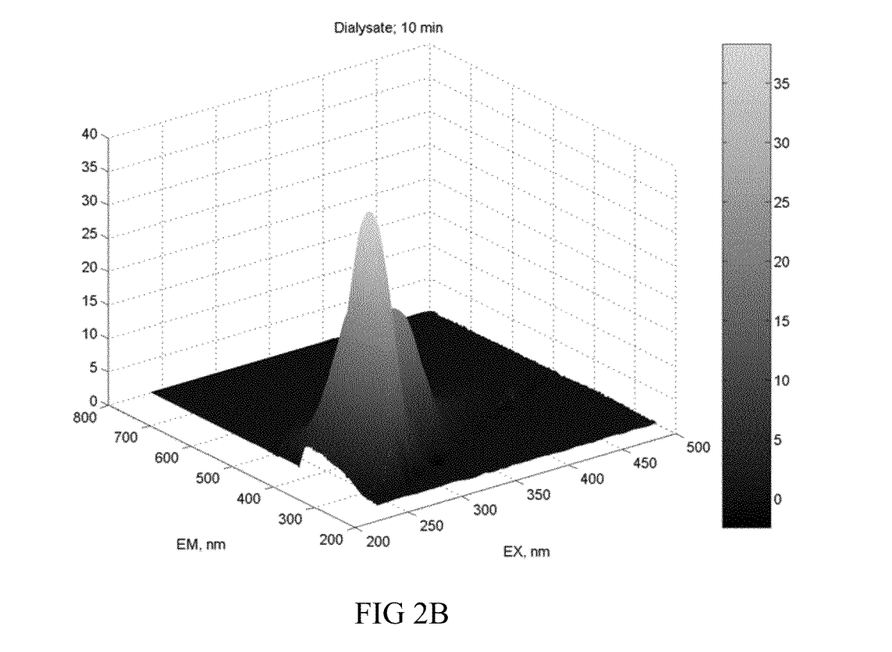
Figure 2C:
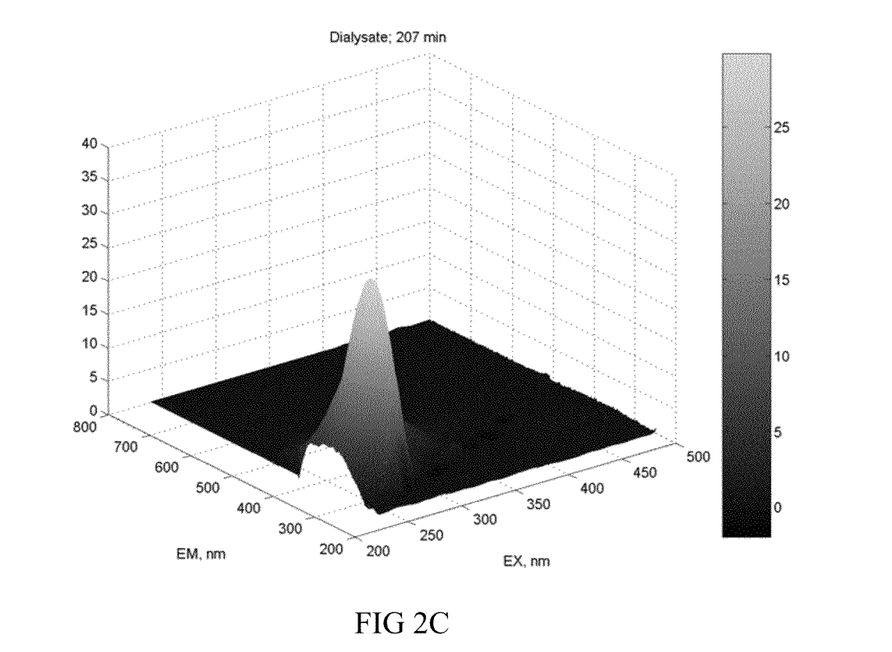

Results: FIG. 2 illustrates the examples of 3D fluorescence spectra obtained over the excitation wavelength range of 240-500 nm and emission wavelength range of 250-800 nm (A) on the pure dialysate sample; (B) on the spent dialysate sample taken at 10 min after the start of a dialysis session; and (C) on the spent dialysate sample taken at 240 min after the start of a dialysis session. Some distinctive fluorescence maxima at specific regions are clearly seen. Moreover, the fluorescence amplitude is proportional to the content of eliminated uremic toxins in the spent dialysate being higher in the beginning of the dialysis treatment (10 min) and lower at the end of the dialysis (207 min) at specific regions of the fluorescence spectra.

The linear relationship analysis for B2M and IS, utilizing fluorescence values from the new method and concentrations from the laboratory, resulted correlation plots as shown in FIGS. 3A-B and 4A-B. This led to specific models which enabled transform the optical measurements into the concentration values.

Figure 3A:
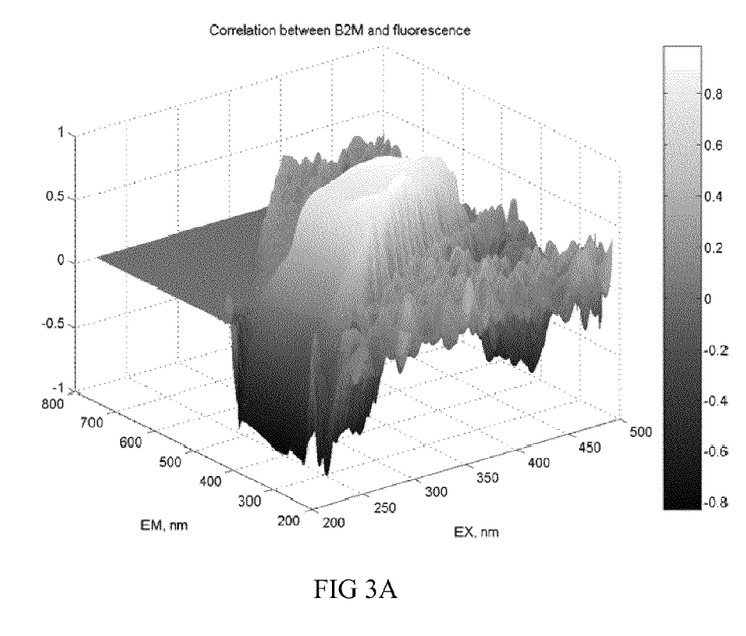
FIG. 3 shows the linear relationship between beta2-microglobulin (B2M) concentration measured at the laboratory and by the new method as: (A) correlation coefficient between B2M concentration measured at the laboratory and fluorescence signal as a 3D plot over a range of excitation wavelengths (EX) 220-500 nm and over a range of emission wavelengths (EM) 220-800 nm; (B) correlation coefficient between B2M concentration measured at the laboratory and fluorescence signal as a 2D plot for a single excitation wavelength EX=370 nm and over a range of emission wavelengths (EM) 220-700 nm; (C) plot for B2M concentration measured by the new method and at the laboratory at the fixed emission and excitation wavelengths (EX=370 nm, EM=456 nm).
Figure 3B:
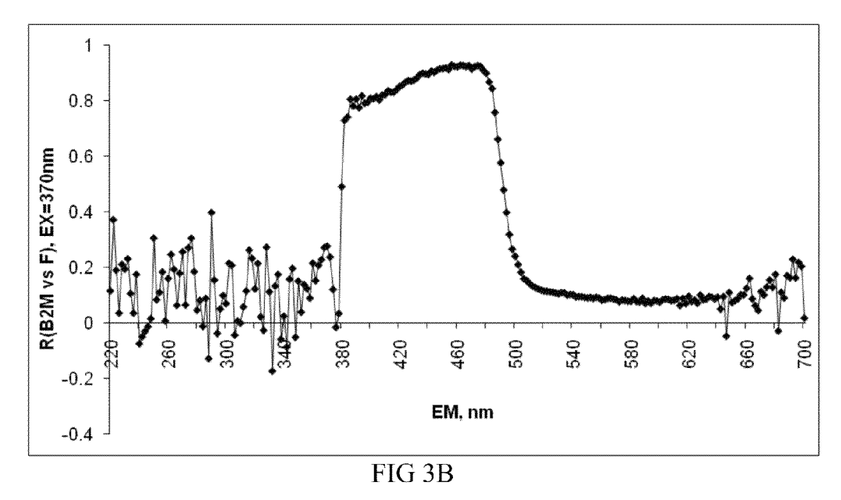
Figure 3C:
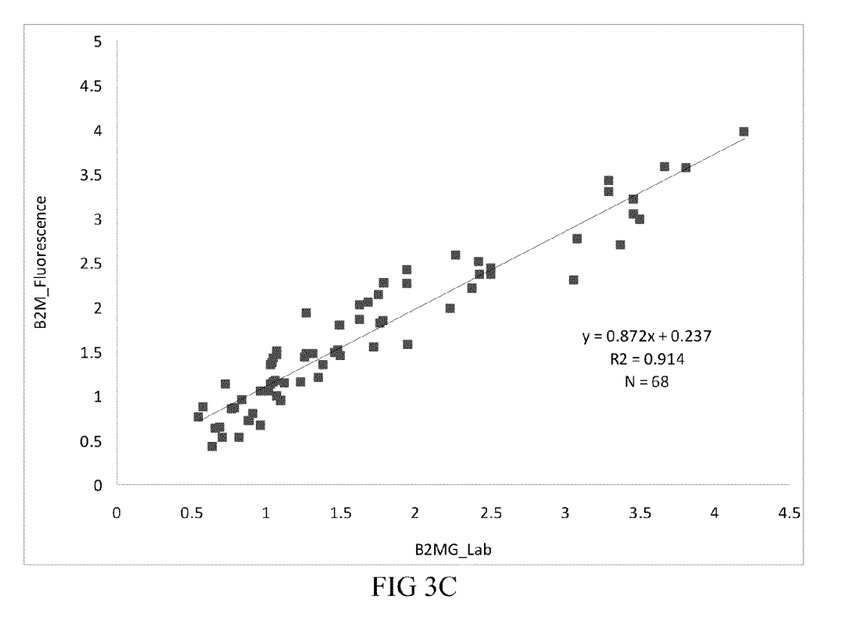
Figure 4A:
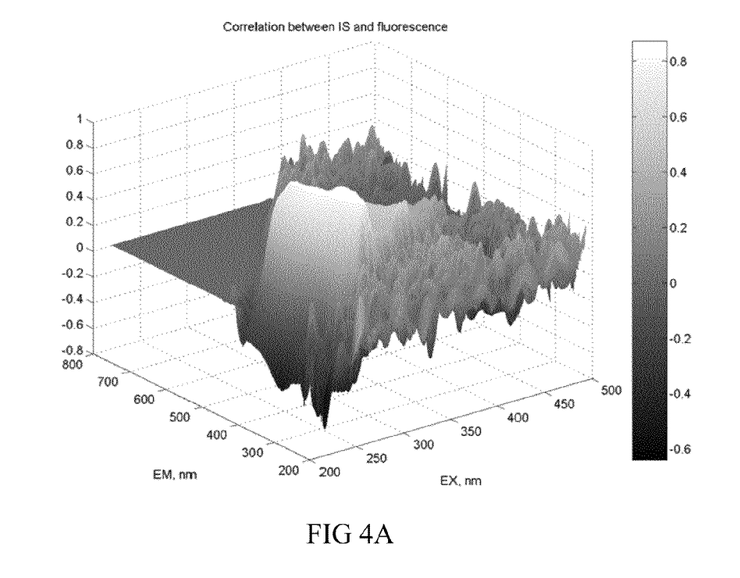
FIG. 4 shows the linear relationship between indoxyl sulfate (IS) concentration measured by the new method and by HPLC at the laboratory as: (A) correlation coefficient between IS concentration measured at the laboratory and fluorescence signal as a 3D plot over a range of excitation wavelengths (EX) 220-500 nm and over a range of emission wavelengths (EM) 220-800 nm; (B) correlation coefficient between IS concentration measured at the laboratory and fluorescence signal as a 2D plot for a single excitation wavelength EX=300 nm and over a range of emission wavelengths (EM) 220-590 nm; (C) plot for the IS concentrations measured by the new method and at the laboratory at the fixed emission and excitation wavelengths (EX=300 nm, EM=358 nm).
Figure 4B:
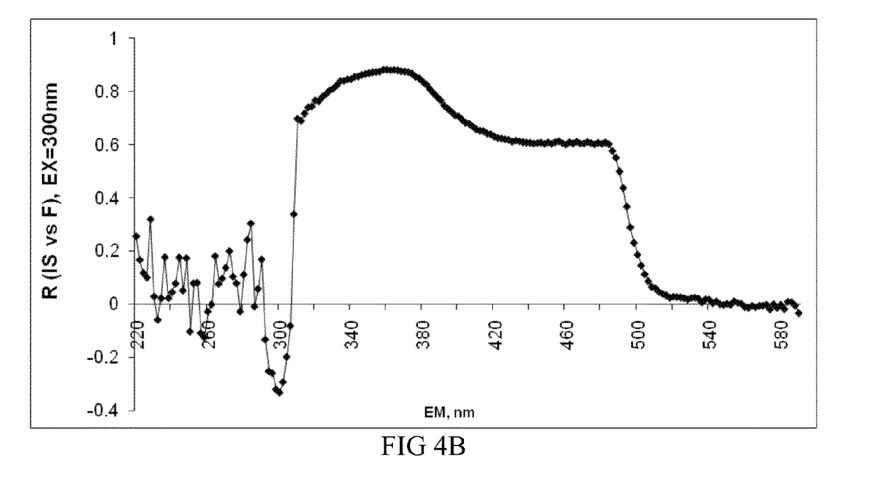
Figure 4C:
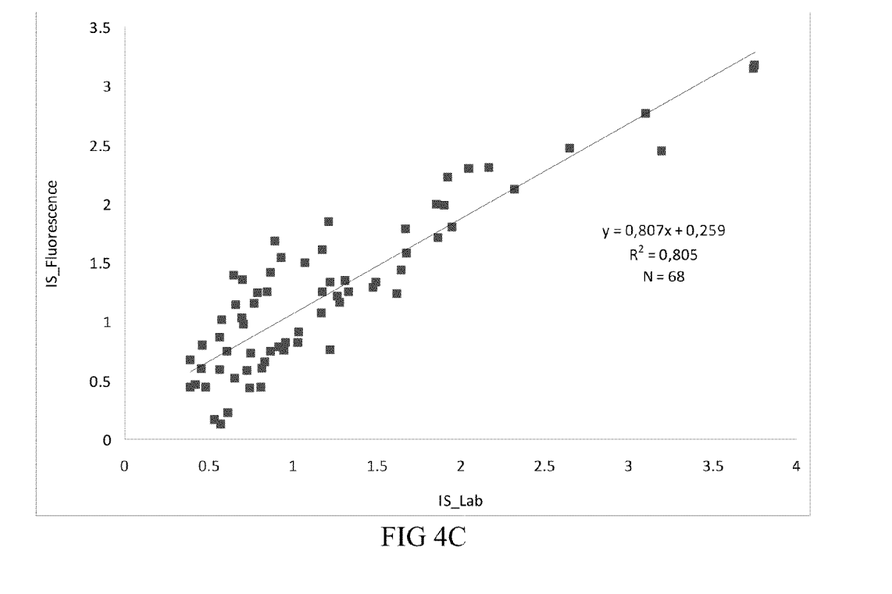

The determined values of B2M and IS concentrations by the new method, obtained by specific models, including a unique set of optical spectral components at certain wavelengths, compared to the values measured at the laboratory by biochemical methods or HPLC in the spent dialysate, are presented on FIGS. 3C and 4C.

Accuracy (BIAS) was calculated for the new method as $$BIAS = \frac{\sum_{i=1}^{N} e_i}{N} \tag{1}$$

where $e_i$ is the i-th residual and N is the number of observations. The i-th residual was obtained as the difference between laboratory and optically determined concentration values for the i-th measurement.

Precision (SE) was calculated for the new method as $$SE = \sqrt{\frac{\sum_{i=1}^{N}(e_i - BIAS)^2}{N}} \tag{2}$$

Table 1 summarises all results about the B2M and IS concentrations as mean and standard deviation values (Mean+/−SD) from the standardised methods (Lab) and from the new method (F). The linear correlation coefficient (R) and the R-squared value (R2) between the uremic toxins concentration from the optical method and concentration measured at the laboratory, the accuracy (BIAS) and precision (SE) for the different methods to measure concentration of B2M and IS, are also given.

Table 1: Summary results about the concentration mean and standard deviation values (Mean+/−SD) from the standardised methods (Lab) and new method (F), linear correlation coefficient (R) and the R-squared value (R2) between the uremic toxins concentration from the optical method and concentration measured at the laboratory, the accuracy (BIAS) and precision (SE) for the different methods to measure concentration of B2M and IS.

|  | B2M mg/L | IS mg/L |
| --- | --- | --- |
| N | 68 | 68 |
| Lab (Mean +/− SD) | 1.69 +/− 0.94 | 1.22 +/− 0.77 |
| F (Mean +/− SD) | 1.71 +/− 0.86 | 1.24 +/− 0.69 |
| R | 0.96 | 0.90 |
| R2 | 0.91 | 0.81 |
| BIAS [mg/L] | 0.02 | 0.02 |
| SE [mg/L] | 0.28 | 0.34 |

As seen from the Table 1 determination of B2M and IS concentration can be done with satisfactory accuracy and precision applying the novel method.

As an example for clinical application, the concentration of B2M from optical measurements is utilized below to calculate the dialysis dose for B2M, being representative in its kinetic behaviour of other MM and peptides of similar size.

The dialysis dose for the B2M from blood, spKt/Vb_B2M and eKt/Vb_B2M, can be calculated using the pre- and post-dialysis blood B2M concentrations ($C_0$ and $C_t$). The single pool volume Kt/V, spKt/Vb_B2M was calculated according to the formula proposed by Casino et al 2010, as $$spKt/Vb\_B2M = 6.12 \frac{UF}{W} \left[ \frac{1 - \ln\frac{C_t}{C_0}}{\ln\left(1 + 6.12\frac{UF}{W}\right)} \right] \tag{3}$$

where UF is the total ultrafiltration in kg and W is the patient's dry body weight in kg.

The equilibrated Kt/V, eKt/Vb_B2M, taking account post-dialysis B2M rebound, was obtained according to the formula proposed by Tattersall et al 2007, as:

$$eKt/Vb\_B2M = spKt/V_{\beta 2m} * T_d/(T_d + 110) \tag{4}$$

where Td is the dialysis session length.

For determination of the dialysis dose for B2M from the optical method, instead of the pre- and post-dialysis blood B2M concentrations, the fluorescence value in the beginning, F0 (10 min dialysate sample) and the fluorescence value at the end of dialysis, Ft, were utilized. The single pool volume Kt/V from the fluorescence measurements, spKt/Vf_B2M was calculated as $$spKt/Vf\_B2M = 6.12 \frac{UF}{W} \left[ \frac{1 - \ln\frac{F_t}{F_0}}{\ln\left(1 + 6.12\frac{UF}{W}\right)} \right] \tag{5}$$

The equilibrated Kt/V from the fluorescence measurements, eKt/Vf_B2M was calculated according to equation 4.

Table 2 summarises all results about the dialysis dose for the B2M as spKt/V_B2M and eKt/V_B2M calculated using the pre- and post-dialysis blood B2M concentrations and the fluorescence values from totally 19 HDF sessions. The linear correlation coefficient (R) and the R-squared value (R2) between the dialysis dose for B2M from the optical method and dialysis dose for B2M from the blood concentrations are given. The accuracy (BIAS) and precision (SE) for the optical method was calculated using dialysis dose for the B2M from blood as reference after bias correction.

Table 2: Summary of dialysis dose as spKt/V_B2M and eKt/V_B2M, calculated using the pre- and post-dialysis blood B2M concentrations (Blood) and the fluorescence values (F), the linear correlation coefficient (R) and the R-squared value (R2) between the dialysis dose for B2M from the optical method and from the blood concentrations, the accuracy (BIAS) and precision (SE) for the optical method.

|  | spKt/V_B2M | eKt/V_B2M |
| --- | --- | --- |
| N (HDF sessions) | 19 | 19 |
| Blood (Mean +/− SD) | 1.63 +/− 0.18 | 1.11 +/− 0.13 |
| F (Mean +/− SD) | 1.63 +/− 0.21 | 1.11 +/− 0.14 |
| R | 0.74 | 0.73 |
| R2 | 0.55 | 0.53 |
| BIAS | 0.00 | 0.00 |
| SE | 0.15 | 0.10 |

Figure 5:
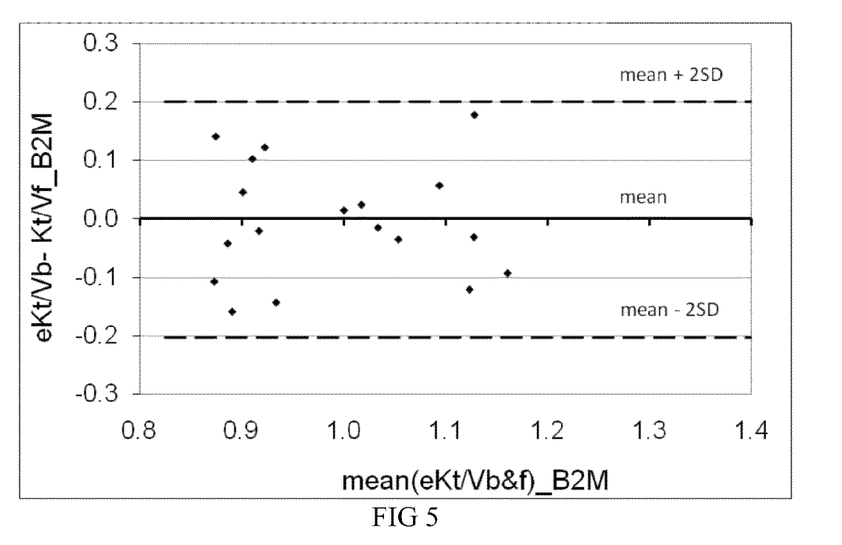
FIG. 5 shows a Bland-Altman plot of the estimated parameter eKt/V_B2M for 8 patients as the differences between eKt/Vb_B2M and eKt/Vf_B2M (number of HDF sessions N=19) plotted against mean_eKt/V(b&f)_B2M after bias correction.
Figure 6:
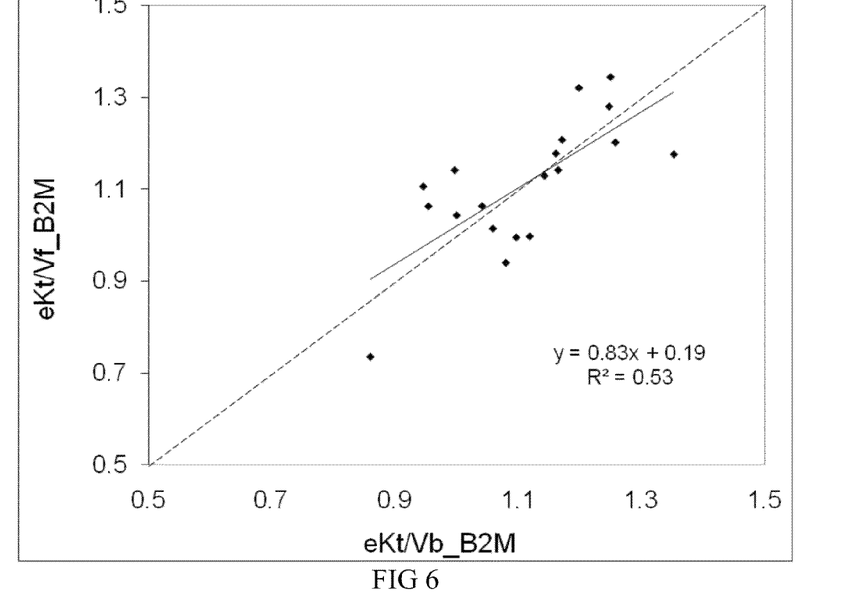
FIG. 6 illustrates the dialysis dose for B2M as eKt/Vf_B2M from the optical method measured in the spent dialysate plotted against eKt/Vb_B2M estimated using the blood samples (number of HDF sessions N=19). A line of unity as a dashed line is also shown.

FIG. 5 presents a comparison as a Bland-Altman plot of the estimated parameter eKt/V_B2M for all 8 patients as the differences between eKt/Vb_B2M and eKt/Vf_B2M (number of HDF sessions N=19) plotted against mean_eKt/V (b&f)_B2M after bias correction. FIG. 6 illustrates the dialysis dose for B2M as eKt/Vf_B2M from the optical method measured in the spent dialysate plotted against eKt/Vb_B2M estimated using the blood samples (number of HDF sessions N=19). A line of unity as a dashed line is also shown.

The results show good agreement between the dialysis dose estimated for B2M from the blood samples and from the spent dialysate samples by the fluorescence.

As the next example for clinical application, the concentration of IS from optical measurements is utilized below to calculate the dialysis dose during a single HDF session for the protein bound uremic toxin IS as: 1) removal rate for IS (RR_IS), and 2) total removed amount for IS (TR_IS). The removal rate for IS (RRd_IS) and total removed amount for IS (TRd_IS), based on IS concentrations in the spent dialysate instead in the blood, were used as the reference to corresponding parameters estimated by the optical method (RRf_IS and TRf_IS), since the elimination rate on blood values could be misleading due to specific kinetic behavior of the protein bound uremic toxins.

The removal rate for IS in the spent dialysis (RRd_IS) was calculated as $$RRd\_IS = \frac{C_0 - C_t}{C_0} * 100\% \quad (6)$$

where $C_0$ and $C_t$ are the spent dialysis IS concentrations from the laboratory in the beginning (10 min dialysate sample) and at the end of dialysis, respectively.

For determination of the dialysis dose for IS from the optical method, instead of the spent dialysis IS concentrations from the laboratory, the corresponding values from the fluorescence measurements, $F_0$ (10 min dialysate sample) and the fluorescence value at the end of dialysis, $F_t$, were utilized.

The total removed IS (TRd_IS) in mg, utilizing the concentration of IS, Dtotal in mg/L, from total dialysate collection, and the total amount of collected dialysate, Wtotal in kg, is given by $$TRd\_IS = D_{total} * W_{total} \quad (7)$$

assuming that, for the spent dialysate, 1 kg=1 L. For determination of the total removed IS from the optical method (TRf_IS) the corresponding value for Dtotal in mg/L, estimated by the fluorescence measurements, were utilized.

Table 3 summarises all results about the dialysis dose for the IS as RR_IS and TR_IS calculated using the spent dialysis IS concentrations from the laboratory in the beginning (10 min dialysate sample) and at the end of dialysis, and corresponding values from the fluorescence measurements. The linear correlation coefficient (R) and the R-squared value (R2) between the dialysis dose for IS from the optical method and dialysis dose for IS from the blood concentrations are given. The accuracy (BIAS) and precision (SE) for the optical method was calculated using dialysis dose for the IS from blood as reference after bias correction.

Table 3: Summary of the dialysis dose for the IS as RR_IS and TR_IS calculated using the spent dialysis IS concentrations from the laboratory in the beginning (10 min dialysate sample) and at the end of dialysis, and corresponding values from the fluorescence measurements (F), the linear correlation coefficient (R) and the R-squared value (R2) between the dialysis dose for IS from the optical method and from the spent dialysate concentrations, the accuracy (BIAS) and precision (SE) for the optical method.

|  | RR_IS, % | TR_IS, mg |
| --- | --- | --- |
| N (HDF sessions) | 19 | 20 |
| Dialysate (Mean +/− SD) | 51.4 +/− 11.8 | 163 +/− 90 |
| F (Mean +/− SD) | 51.4 +/− 10.6 | 163 +/− 90 |
| R | 0.92 | 0.93 |
| R2 | 0.85 | 0.87 |
| BIAS | 0.00 | 0.00 |
| SE | 4.60 | 33.3 |

Figure 7:
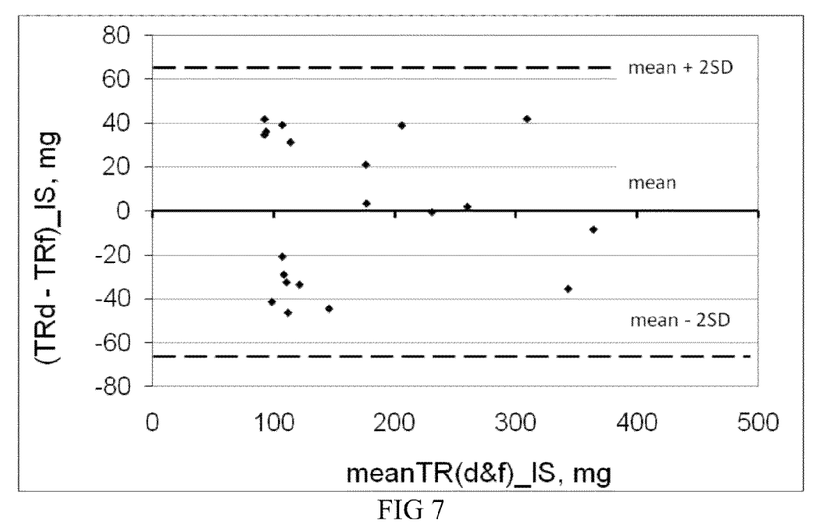
FIG. 7 shows a Bland-Altman plot of the estimated parameter TR_IS for 8 patients as the differences between TRd_IS and TRf_IS (number of HDF sessions N=20) plotted against mean_TR(d&f)_IS after bias correction.
Figure 8:
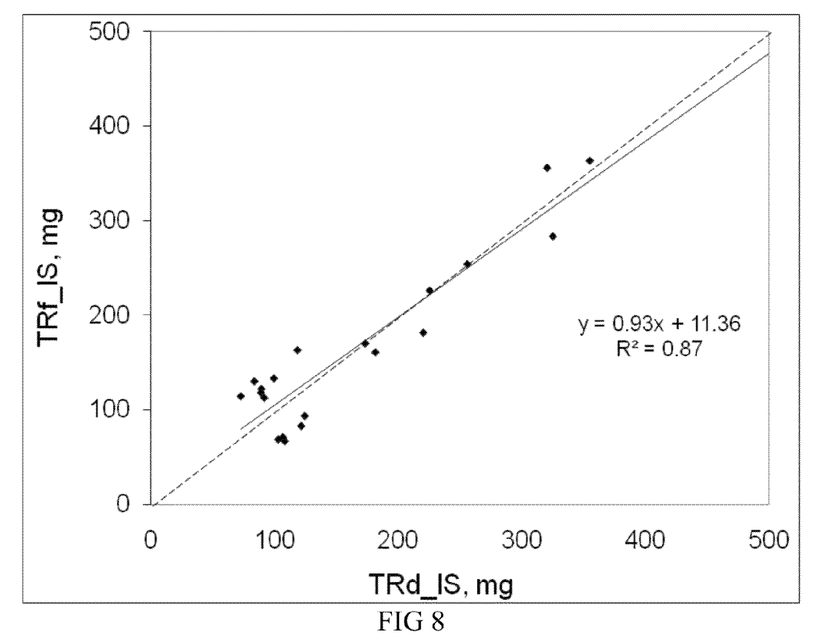
FIG. 8 illustrates the dialysis dose for IS as TRf_IS from the optical method plotted against TRd_IS from laboratory estimated using the spent dialysate samples (number of HDF sessions N=20). A line of unity as a dashed line is also shown.

FIG. 7 presents a comparison as a Bland-Altman plot of the estimated parameter TR_IS for all 8 patients as the differences between TRd_IS and TRf_IS (number of HDF sessions N=20) plotted against mean_TR(d&f)_IS after bias correction. FIG. 8 illustrates the dialysis dose for IS as TRf_IS from the optical method plotted against TRd_IS from laboratory estimated using the spent dialysate samples (number of HDF sessions N=20). A line of unity as a dashed line is also shown.

The results show good agreement between the dialysis dose estimated for IS from the spent dialysate samples by the laboratory methods and from the spent dialysate samples by the fluorescence.

Figure 9:
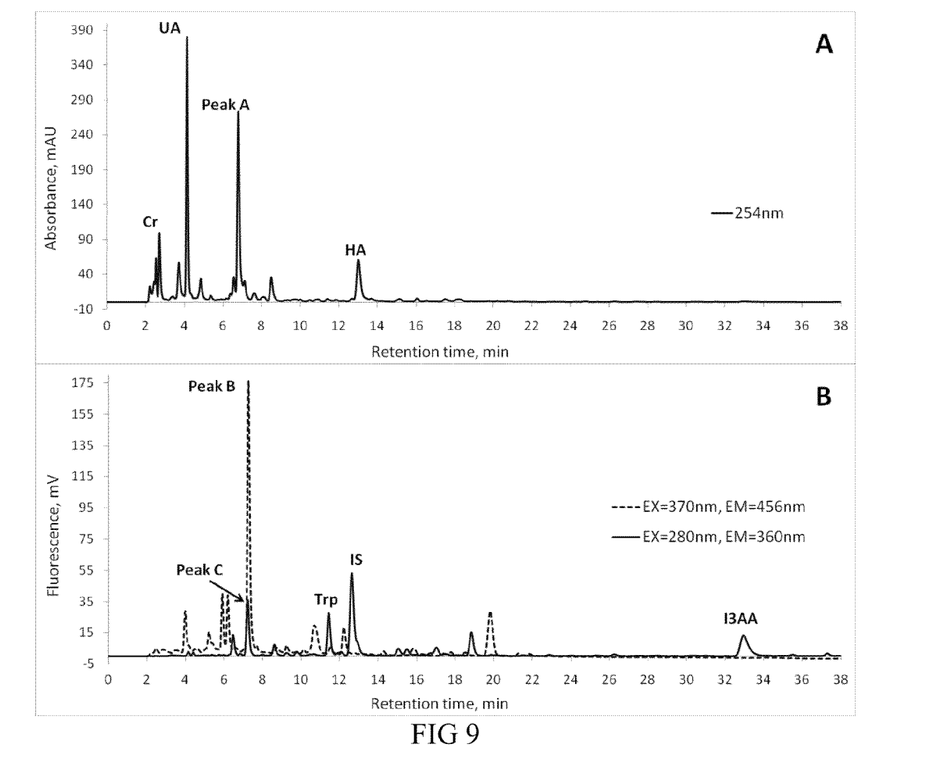
FIG. 9 presents HPLC profiles of a spent dialysate sample for: (A) measured absorbance at the wavelength of 254 nm, and (B) measured fluorescence at the two fixed emission and excitation wavelengths (EX=370 nm, EM=456 nm, and EX=280 nm, EM=360 nm). A number of higher prevalent peaks representing chromophores-fluorofores removed during a dialysis session can be observed. Some HPLC peaks were identified, such as creatinine (Cr), uric acid (UA), hippuric acid (HA), trypthophane (Trp), indoxyl sulfate (IS), indol-3-acetic acid (I3AA). 3 prevalent, but non-identified peaks—Peak A, Peak B and Peak C—were detected at different wavelengths.

HPLC profiles of the spent dialysate samples were analysed in order to identify the origin of the measured optical signal. FIG. 9 presents HPLC profiles of a spent dialysate sample for: (A) measured absorbance at the wavelength of 254 nm, and (B) measured fluorescence at the two fixed emission and excitation wavelengths (EX=370 nm, EM=456 nm, and EX=280 nm, EM=360 nm). A number of higher prevalent peaks can be observed, representing solutes containing chromophores-fluorophores, and removed during a dialysis session. Some HPLC peaks were identified, such as creatinine (Cr), uric acid (UA), hippuric acid (HA), tryptophane (Trp), indoxyl sulfate (IS), indol-3-acetic acid (I3AA). Moreover, 3 prevalent, but non-identified peaks—Peak A, Peak B and Peak C—were detected at different wavelengths. The HPLC profiles of the spent dialysate samples demonstrate selectivity for different solutes at different wavelengths. By this way, appropriate wavelength choice for the optical method enables to determine specific uremic toxins.

Although this invention is described with respect to a set of aspects and embodiments, modifications thereto will be apparent to those skilled in the art. The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

PATENT REFERENCES

U.S. Pat. No. 6,666,840, Method for determining waste products in the dialysis liquid in dialysis treatment, FALKVALL T et al.
WO9819592, Dialysis monitoring method and apparatus, KEMENY G J, MAYNARD J D.
U.S. Pat. No. 5,886,347, Analytical method for multi-component aqueous solutions and apparatus for the same, INOUE M.
RU212029 C1, "Way of analysis of liquid biological medium in process monitoring", VASILEVSKIJ A M et al.
WO2009071102A1, Ivo Fridolin, Jana Jerotskaja, Kai Lauri, Merike Luman. Optical method and device for measuring concentrations of substances in biological fluids. 4 Dec. 2007.
EE201000049, Ivo Fridolin, Jana Jerotskaja, Kai Lauri, Merike Luman. Optical method and device for quantitative concentration measurements of compounds in the biological fluids. 27 May 2010.
WO2005111586, Babichenko Sergei, Erme Enn, Ivkina Tatjana, Poryvkina Larisa, Sominsky Vitaly. A portable device and method for on-site detection and quantification of drugs, 13 May 2004.
US20050079628, Nekrasov Viktor et al, Method for assaying multi-component mixtures, 9 Oct. 2003.

NON-PATENT REFERENCES

Casino F G, Pedrini L A, Santoro A, Mandolfo S, David S, De Cristofaro V, Teatini U, Lomonte C, Lopez T. A simple approach for assessing equilibrated Kt/V beta 2-M on a routine basis. Nephrol Dial Transplant. 2010 September; 25(9):3038-44.
Dhondt, A. W., R. C. Vanholder, et al. (2003). "Studies on dialysate mixing in the Genius (R) single-pass batch system for hemodialysis therapy." Kidney International 63(4): 1540-1547.
ERA-EDTA (2002). "EBPG—European Best Practice Guidelines: SECTION II. Haemodialysis adequacy II.2 Haemodialysis dose quantification: middle molecules (MM)." Nephrology Dialysis Transplantation 17 [Suppl 7]: 21-23.
Fridolin, I., M. Magnusson, et al. (2002). "On-line monitoring of solutes in dialysate using absorption of ultraviolet radiation: technique description." The International Journal of Artificial Organs 25(8): 748-761.
Tattersall, J., A. Martin-Malo, et al. (2007). "EBPG guideline on dialysis strategies." Nephrology Dialysis Transplantation 22: 5-21.
Tattersall J. Clearance of beta-2-microglobulin and middle molecules in haemodiafiltration. Contrib Nephrol. 2007; 158:201-9.
Trifonov, V. (2009). Application of CLS and ILS modeling for analysis of uremic toxins, Supervisor I. Fridolin. Biomedical Engineering Centre, Technomedicum. Tallinn, Tallinn University of Technology. MSc Diploma work.
Uhlin, F., I. Fridolin, et al. (2005). "Estimating total urea removal and protein catabolic rate by monitoring UV absorbance in spent dialysate." Nephrol Dial Transplant. November 20((11)): 2458-2464.
Uhlin, F., L. G. Lindberg, et al. (2005). Total Removed Uric Acid During Dialysis Estimated by On-line Ultra Violet Absorbance in the Spent Dialysate. 3rd European Medical & Biological Engineering Conference, EMBEC'05, Prague, Czech Republic, IFMBE Proceedings 11, CD-ISSN: 1727-1983, 6 pages, IFMBE Proceedings.
Vanholder, R., R. De Smet, et al. (2003). "Review on uremic toxins: classification, concentration, and interindividual variability." Kidney International 63(5): 1934-1943.
Wishart D S, Knox C, et al. (2009). "HMDB: a knowledgebase for the human metabolome." Nucleic Acids Res. 37((Database issue)): D603-610.
Yavuz, A., et al. (2005). "Uremic toxins: a new focus on an old subject." Semin Dial (May-June; 18(3)): 203-11.

The invention claimed is:

1. A method for determining content of the middle and protein bound uremic toxins in a biological fluid comprising:
   a. introducing a flowing stream of a sample of the biological fluid through a fluorimetrical flow-cuvette;
   b. applying light with predetermined wavelengths to the sample and recording an fluorescence signal of the sample;
   c. calculating a concentration of the substance in the sample from a transforming function by executing a transforming function in the form "uremic toxin concentration [mg/L]=F*Slope+Intercept", where F notes a fluorescence signals; and
   d. outputting the concentration of the substance to a display device or to a printer.

2. The method according to claim 1, wherein an excitation wavelength from a light source is in the wavelength range of 190-890 nm.

3. The method according to claim 1, wherein an emission wavelength detected by a light detector is operating in wavelength range of 190-900 nm.

4. The method according to claim 1, wherein the substance is β2-micro globulin.

5. The method according to claim 1, wherein a light source is operating in the wavelength range of 360-380 nm, and a fluorescence light detector is operating in the wavelength range of 440-470 nm, suitable for beta2-microglobulin measurements.

6. The method according to claim 1, wherein the substance is indoxyl sulfate.

7. The method as in claim 1, wherein-a light source is operating in the wavelength range of 290-310 nm, and a fluorescence light detector in the wavelength range of 340-370 nm, suitable for indoxyl sulfate measurements.

8. The method according to claim 1, comprising dropping the sample of the biological fluid onto in-vitro cuvette.

* * * * *